(12) United States Patent
Arsenault et al.

(10) Patent No.: US 7,203,276 B2
(45) Date of Patent: Apr. 10, 2007

(54) X-RAY SCATTER IMAGE RECONSTRUCTION BY BALANCING OF DISCREPANCIES BETWEEN DETECTOR RESPONSES, AND APPARATUS THEREFOR

(75) Inventors: Paul Jacob Arsenault, Fredericton (CA); Esam Hussein, Fredericton (CA)

(73) Assignee: University of New Brunswick, Fredericton, N.B. (CA)

( * ) Notice: Subject to any disclaimer, the term of this patent is extended or adjusted under 35 U.S.C. 154(b) by 37 days.

(21) Appl. No.: 11/189,950

(22) Filed: Jul. 27, 2005

(65) Prior Publication Data

US 2006/0043310 A1    Mar. 2, 2006

Related U.S. Application Data

(60) Provisional application No. 60/604,684, filed on Aug. 27, 2004.

(51) Int. Cl.
*G01N 23/201* (2006.01)

(52) U.S. Cl. ............................................. 378/87; 378/57
(58) Field of Classification Search ..................... 378/9, 378/50, 51, 54, 57, 62, 87; 250/393
See application file for complete search history.

(56) References Cited

U.S. PATENT DOCUMENTS

| | | |
|---|---|---|
| 3,202,822 A | 8/1965 | Kehler |
| 3,809,904 A | 5/1974 | Clarke et al. |
| 3,840,746 A | 10/1974 | Kehler |
| 4,123,654 A | 10/1978 | Reiss et al. |
| 4,228,351 A | 10/1980 | Snow et al. |
| 4,375,695 A | 3/1983 | Harding et al. |
| 4,423,522 A | 12/1983 | Harding |

(Continued)

FOREIGN PATENT DOCUMENTS

CA          1076712          4/1980

(Continued)

OTHER PUBLICATIONS

1. Hussein, E.M.A.; Meneley, D.A. and Banerjee, S.; "On the Solution of the Inverse Problem of Radiation Scattering Imaging"; published in Nuclear Science and Engineering, vol. 92, pp. 341-349, 1986.

(Continued)

*Primary Examiner*—Courtney Thomas
(74) *Attorney, Agent, or Firm*—Mario Theriault

(57) ABSTRACT

The present invention pertains to a method and an apparatus to generate a density image of an object using fan or cone beams of radiation and collimated detectors on one side of the object. The method consists of irradiating an object with a plurality of pairs of non-parallel radiation beams wherein the beams in each pair intersect a same segment along the axis of the detector. Compton-scattering radiation from the beams are then measured, and corrected attenuation coefficients along each beam are obtained. This latter step is effected by taking a first ratio of detector measurements for the beams in each pair; comparing the first ratio with a second ratio of corresponding calculated detector measurements and balancing discrepancies between the first and second ratios in a forward-inverse numerical analysis algorithm. Taking ratios of attenuation coefficients along related incident beams eliminates non-linearity problems whereby the aforesaid algorithm can be solved.

19 Claims, 3 Drawing Sheets

U.S. PATENT DOCUMENTS

| | | | |
|---|---|---|---|
| 4,558,220 A | 12/1985 | Evans | |
| 4,578,580 A | 3/1986 | Smith, Jr. | |
| 4,768,214 A | 8/1988 | Bjorkholm | |
| 4,785,401 A | 11/1988 | Harding et al. | |
| 4,799,247 A | 1/1989 | Annis et al. | |
| 4,850,002 A | 7/1989 | Harding et al. | |
| 4,870,670 A | 9/1989 | Geus | |
| 4,884,289 A | 11/1989 | Glockmann et al. | |
| 4,887,285 A | 12/1989 | Harding et al. | |
| 4,896,342 A | 1/1990 | Harding | |
| 4,956,856 A | 9/1990 | Harding | |
| 5,023,895 A | 6/1991 | McCrosket et al. | |
| 5,033,073 A | 7/1991 | Friddell | |
| 5,040,200 A | 8/1991 | Ettinger et al. | |
| 5,070,455 A | 12/1991 | Singer et al. | |
| 5,125,015 A | 6/1992 | Shimoni et al. | |
| 5,125,017 A | 6/1992 | Lempriere | |
| 5,150,395 A | 9/1992 | Kosanetzky et al. | |
| 5,179,581 A | 1/1993 | Annis | |
| 5,247,560 A | 9/1993 | Hosokawa et al. | |
| 5,247,561 A | 9/1993 | Kotowski | |
| 5,260,982 A | 11/1993 | Fujii et al. | |
| 5,313,511 A | 5/1994 | Annis et al. | |
| 5,367,552 A | 11/1994 | Peschmann | |
| 5,420,905 A | 5/1995 | Bertozzi | |
| 5,428,657 A | 6/1995 | Papanicolopoulos | |
| 5,430,787 A | 7/1995 | Norton | |
| 5,524,133 A | 6/1996 | Neale et al. | |
| 5,533,080 A | 7/1996 | Pelc | |
| 5,590,169 A | 12/1996 | Monteiro | |
| 5,600,700 A | 2/1997 | Krug et al. | |
| 5,602,893 A | 2/1997 | Harding | |
| 5,642,393 A | 6/1997 | Krug et al. | |
| 5,642,394 A | 6/1997 | Rothschild | |
| 5,692,029 A | 11/1997 | Husseiny et al. | |
| 5,696,806 A | 12/1997 | Grodzins et al. | |
| 5,703,923 A | 12/1997 | Bardash | |
| 5,729,582 A | 3/1998 | Ham et al. | |
| 5,838,758 A | 11/1998 | Krug et al. | |
| 5,930,326 A | 7/1999 | Rothschild et al. | |
| 5,940,468 A | 8/1999 | Huang et al. | |
| 5,970,116 A | 10/1999 | Dueholm et al. | |
| 5,974,111 A | 10/1999 | Krug et al. | |
| 6,018,562 A | 1/2000 | Willson | |
| 6,052,433 A | 4/2000 | Chao | |
| 6,094,470 A | 7/2000 | Teller | |
| 6,359,961 B1* | 3/2002 | Aufrichtig et al. | 378/41 |
| 6,556,653 B2 | 4/2003 | Hussein | |
| 6,563,906 B2 | 5/2003 | Hussein et al. | |
| 6,711,232 B1 | 3/2004 | Janik | |
| 6,856,667 B2 | 2/2005 | Ellengogen | |
| 6,879,657 B2 | 4/2005 | Hoffman | |
| 2003/0016783 A1* | 1/2003 | Grodzins et al. | 378/57 |
| 2004/0079232 A1 | 4/2004 | Groh et al. | |

FOREIGN PATENT DOCUMENTS

| | | |
|---|---|---|
| CA | 1101133 | 5/1981 |
| CA | 1135878 | 11/1982 |
| CA | 1256595 | 6/1989 |
| CA | 1304834 | 7/1992 |
| CA | 2381398 | 2/2001 |
| JP | 0201341 | 9/1987 |

OTHER PUBLICATIONS

2. Hussein, E.M.A.; "Compton Scatter Imaging Systems" published in Bioinstrumentation: Research, Developments and Applications, Butterworths Publ. Stoneham, MA, D.L. Wise, Ed., Chapter 35 pp. 1053-1086, 1990.

3. Unknown author: "Single Photon Emission Computed Tomography" published on the Internet as course material at http://www.imt.liu.se/gu/IMTKurser/tbmt02/Toc.html, in a Web site entitled Medicinsk Teknik, Chapter 5, pp. 89-103, 2000.

4. Mathias, Robert; "The Basics of Brain Imaging"; published in NIDA Notes, vol. 11, 1996.

6. Hussein, E.M.A. and Whynot, T.M. "A Compton Scattering Method for Inspecting Concrete Structures" published in Nuclear Instruments and Methods in Physics Research A 283, pp. 100-106; North-Holland, Amsterdam, 1989.

7. Lale, P.G. "The Examination of Internal Tissues by High-Energy Scattered X-Radiation", published by the Physics Department, Guy's Hospital, London, S.E.1, United Kingdom, pp. 510-517, 1968.

8. Al-Bahri, J.S. and Spyrou, N.M., "Electron Density of Normal and Pathological Breast Tissues Using a Compton Scattering Technique" published by the Department of Physics, University of Surrey, Guildford, Surrey GU2 5XH, U.K., pp. 1677-1684, 1997.

9. Clarke, R.L., and Van Dyk, G.; "A New Method for Measurement of Bone Mineral Content Using Both Transmitted and Scattered Beams of Gamma-Rays" Published in Phys. Med. Biol., vol. 18, No. 4, pp. 532-539, 1973.

10. Kaufman, Leon; Gamsu, Gordon; Savoca, Charles; Swann, Sybil; Murphey, Louis; Hruska, Bernard; Palmer, David; Ullman, John; "Measurement of Absolute Lung Density by Compton-Scatter Densitometry", Published in IEE Transactions on Nuclear Science, vol. NS-23, No. 1, pp. 599-605, 1976.

11. Huddleston, A.L. and Bhaduri, D., "Compton Scatter Densitometry in Cancellous Bone" published in Phys. Med. Biol. vol. 24, No. 2, pp. 310-318, 1979.

12. Huddleston, Alan L. and Sackler, Jay. P., "The Determination of Electron Density by the Dual-Energy Compton Scatter Method", published in Medical Physics vol. 12(1) pp. 13-19, 1985.

13. Balogun, F.A. and Spyrou, N.M., "Compton Scattering Tomography in the Study of a Dense Inclusion in a Lighter Matrix", published in Nuclear Instruments and Methods in Physics Research vol. B83, pp. 533-538, 1993.

14. Arendtsz, Nina V. and Hussein, Esam M.A., "Energy-Spectral Compton Scatter Imaging, Part II: Experiments", published in IEEE Transactions on Nuclear Science, vol. 42, No. 6, pp. 2166-2172, 1995.

15. Zhu, P., Peix, G., Babot, D. and Muller, J., "In-Line Density Measurement System Using X-Ray Compton Scattering", published by Butterworth-Heinemann, Great Britain, 1995, (Copyright owner: Elsevier Science Ltd.).

16. Arendtsz, Nina V. and Hussein, Esam M.A., "Energy-Spectral Compton Scatter Imaging, Part I: Theory and Mathematics", published in IEEE Transactions on Nuclear Science, vol. 42, No. 6, pp. 2155-2165, 1995.

17. Briesmeister, Judith F. (Editor), "MCNP A General Monte Carlo N-Particle Transport Code" Version 4B, published by Radiation Safety Information Computational Center, P.O. Box 2008, Oak Ridge, TN, 37831-6362, 1997.

18. Busono, Pratondo and Hussein, Esam M.A. "Algorithms for Density and Composition-Discrimination Imaging for Fourth-Generation CT Systems", Published in Phys. Med. Biol., United Kingdom, vol. 44, pp. 1455-1477, 1999.

19. Alvarez, Robert E. and Macovski, Albert, "Energy-Selective Reconstructions in X-Ray Computerized Tomography", Published In Phys. Med. Biol., vol. 21, No. 5, pp. 733-744, 1976.

20. Guzzardi, R; Mey, M.; and Giuntini, C., "90° Compton Scattering Tomography of the Lung: Detection Characteristics and Correction of the Attenuation", published in The Journal of Nuclear Medicine and Allied Sciences, vol. 24, No. 3-4, pp. 163-169, 1980.

21. Towe, Bruce C. and Jacobs, Alan M., "X-Ray Backscatter Imaging", Published in IEEE Transactions on Biomedical Engineering, vol. BME-28, No. 9, pp. 646-654, 1981.

22. Holt, R.S. "Compton Imaging" published in Endeavour, New Series, vol. 9, No. 2, pp. 97-105, 1985.

23. Morgan, H.M.; Shakeshaft, J.T. and Lillicrap, S.C., "Gamma-Ray Backscatter for Body Composition Measurement", published in (Pergamon) Appl. Radiat. Isot., Great Britain, vol. 49, No. 5/6, pp. 555-557, 1998.

24. Mullin, S.K. and Hussein, E.M.A., "A Compton-Scatter Spectrometry Technique for Flaw Detection", published in Nuclear Instruments and Methods in Physics Research, Section A, pp. 663-667, 1994.

25. Herr, Michael D.; McInerney, Joseph J.; Lamser, Dennis. G; Copenhaver, Gary, L., "A Flying Spot X-Ray System for Compton Backscatter Imaging"; Published in IEEE Transactions on Medical Imaging, vol. 13, No. 3, Sep. 1994.

26. El Khettabi, Faysal; Yaar, Iian, and Hussein, Esam M.A.; "A Three-Dimensional X-Ray Scattering System For Multi-Parameter Imaging of Human Head", Published by the Institute of Physics Publishing, in Physics in Medicine and Biology, vol. 48, pp. 3445-3458, 2003.

27. El Khettabi, Faysal, and Hussein, Esam M.A.; "An Inverse Problem for Three-Dimensional X-Ray Scatter/ Transmission Imaging", published by the Institute of Physics Publishing, in Inverse Problems, pp. 477-497, 2003.

28. El Khettabi, Faysal; Hussein, Esam M.A., and Jama, Hassan A., "A Nonrotating Multiparameter 3-D X-Ray Imaging System- Part I: Modeling and Reconstruction", published in IEEE Transactions on Nuclear Science, vol. 51, No. 3, pp. 641-647, Jun. 2004.

29. Jama, Hassan A.; Hussein, Esam M.A.; and El Khettabi, Faysal; "A Nonrotating Multiparameter 3-D X-Ray Imaging System—Part II: Design and Experiments", published in IEEE Transactions on Nuclear Science, vol. 51, No. 3, pp. 648-658, Jun. 2004.

30. Hussein, Esam M.A., Handbook on Radiation Probing, Gauging, Imaging and Analysis, vol. 1: Basics and Techniques, Published by Kluwer Academic Publishers, Norwell, Massachusetts, 2003.

* cited by examiner

X-RAY SCATTER IMAGE RECONSTRUCTION BY BALANCING OF DISCREPANCIES BETWEEN DETECTOR RESPONSES, AND APPARATUS THEREFOR

This application claims the benefit of provisional application Ser. No. 60/604,684, filed Aug. 27, 2004.

FIELD OF THE INVENTION

This invention pertains to x-ray, density-imaging of objects, and more particularly this invention pertains to x-ray, density-imaging using pairs of radiation sources scattering to a same detector, and a method to generate density images comprising the step of balancing discrepancies between detector responses, to overcome non-linearity problems.

BACKGROUND OF THE INVENTION

The use of numerical analysis to determine attenuation of radiation traversing or scattering out of an object has been used since the 1950's. This science has always had its limits and its use remains to the present a considerable challenge. Since powerful computers are now readily available at reasonable price, however, and that the associated mathematics are better understood, numerical calculation methods have been more commonly used to generate density images of objects.

Examples of x-ray imaging systems and methods belonging to the prior art and using numerical analyses are described in the following documents:

U.S. Pat. No. 4,785,401 issued to G. Harding et al. on Nov. 15, 1988;
U.S. Pat. No. 4,887,285 issued to G. Harding et al. on Dec. 12, 1989;
U.S. Pat. No. 5,070,455 issued to J. R. Singer et al. on Dec. 3, 1991;
U.S. Pat. No. 5,696,806 issued to L. Grodzins et al. on Dec. 9, 1997;
U.S. Pat. No. 5,729,582 issued to Y. S. Ham et al. on Mar. 17, 1998;
U.S. Pat. No. 5,838,758 issued to K. D. Krug et al. on Nov. 17, 1998;
U.S. Pat. No. 5,930,326 issued to P. Rothschild et al. on Jul. 27, 1999;
U.S. Pat. No. 6,018,562 issued to P. D. Willson on Jan. 25, 2000;
U.S. Pat. No. 6,052,433 issued to Yong-Sheng Chao on Apr. 18, 2000;
U.S. Pat. No. 6,556,653 issued to E. Hussein on Apr. 29, 2003;

In addition to the above-mentioned prior art documents, the following US Patents are particularly relevant herein as they describe methods and installations using Compton scattering, elaborate mathematical calculations and combination of one radiation source with two detectors or two radiation sources with two detectors. These documents are:

U.S. Pat. No. 3,202,822 issued to P. Kehler on Aug. 24, 1965;
U.S. Pat. No. 3,809,904 issued to R. L. Clarke et al. on May 7, 1974;
U.S. Pat. No. 3,840,746 issued to P. Kehler on Oct. 8, 1974;
U.S. Pat. No. 4,558,220 issued to H. B. Evans on Dec. 10, 1985;
U.S. Pat. No. 4,768,214 issued to P. J. Bjorkholm on Aug. 30, 1988;
U.S. Pat. No. 4,956,856 issued to G. Harding on Sep. 11, 1990;
U.S. Pat. No. 5,729,582 issued to Y. S. Ham et al. on Mar. 17, 1998;
U.S. Pat. No. 5,970,116 issued to S. Dueholm et al. on Oct. 19, 1999;
U.S. Pat. No. 6,094,470 issued to S. Teller on Jul. 25, 2000;
U.S. Pat. No. 6,563,906 issued to E. Hussein et al. on May 13, 2003;

Although several numerical analysis methods are available in the prior art, the forward-inverse numerical analysis algorithm is believed to be the most practical one for radiation-scattering imaging of thick objects. However, it is also believed that this forward-inverse numerical analysis algorithm has been generally overlooked in the past. This numerical analysis method is briefly explained as follows.

Mathematically, radiation-scattering imaging is treated as an inverse problem. To define the inverse problem, one must define the direct or forward problem. The forward problem is the mapping of a set of theoretical parameters into a set of experimentally measurable results. Solving the forward problem is then effected to obtain computed results from given parameters. Obtaining the actual parameters from the detector responses is called solving the inverse problem.

Numerical analysis of radiation-scattering imaging using a forward-inverse numerical analysis algorithm has been previously described by E. M. A. Hussein, D. A. Meneley, and S. Banerjee, in an article entitled: "On the Solution of the Inverse Problem or Radiation Scattering Imaging" published in 1986 in a publication entitled: Nuclear Science and Engineering, issue 92, pages 341–349.

Imaging using scattered radiation, records events that take place deep within an object. In essence, the scattering signal is modulated by the attenuation of radiation as it travels toward the point of scattering and then as it returns to a detector. This renders a nonlinear inverse problem, since the attenuation process is exponential in nature, while the scattering process is linear.

The challenge posed by this non-linearity is best demonstrated by considering the forward problem of scattering from a single voxel. While referring to FIG. 1, it will be appreciated that the scattering of a pencil beam of radiation from a source i, of some incident energy E, is scattered by an angle of 90° within an object having a single voxel j, and is returned to a detector k with an energy E'. The detector response $s_{ijk}$ can be expressed as:

$$s_{ijk} = c_{ijk} \exp\left[-\mu(E)\frac{x}{2}\right] \rho \exp\left[-\mu(E')\frac{y}{2}\right] \quad (1)$$

where ρ refers to density; μ refers to the attenuation coefficient (which is a function of E and ρ); x is the distance travelled by the incident radiation within the voxel along the direction of the incident beam, y is the distance travelled by the scattered beam away from the incident beam, and $c_{ijk}$ is a pre-determined system constant that depends of the probability of scattering, source-voxel-detector geometric arrangement, source intensity, detector efficiency, etc.

To further simplify the problem, let x=y, replace μ(E) and μ(E') with some average value between the two, and assume that μ and ρ are physically related such that μ=σρ, where σ is a known parameter. Equation (1) for a single voxel can now be written as:

$$s_{ijk} = \frac{c_{ijk}}{\sigma} \mu \exp[-\mu x] \quad (2)$$

This equation represents the "forward" problem that relates the problem parameters, attenuation coefficient, to a measurable detector response.

This forward model demonstrates clearly the competition between the linear term (scattering), which increases with increasing $\mu$ and the exponential term (attenuation) which declines in value with increasing $\mu$.

Therefore, $S_{ijk}$ increases with $\mu$ until it reaches a maximum value at $\mu=x^{-1}$, then it decreases with increasing $\mu$. Upon solving the inverse problem to find the value for $\mu$ at a given value for $s_{ijk}$ two solutions are possible. This simple equation is plotted on a graph in FIG. 2 for various values of x. A dotted line 100 extending across the graph shows the two values of $\mu$ for each value of $s_{ijk}$.

The first solution is for $\mu<x^{-1}$ and the other solution at $\mu>x^{-1}$. A single solution only exists at $\mu x=1$, where $s_{ijk}$ reaches it maximum value, at which point $$x = \frac{1}{\mu},$$

i.e. equal to one mean-free-path (mfp).

It will be appreciated that the linear component of Equation (2) is dominant when the distance travelled is less than the average distance travelled by radiation (<1 mfp), while the exponential component is dominant when the distance travelled is greater than the mfp.

Due to the non-linearity of the forward-inverse problem, direct solution is impractical. Therefore, one or more iterations using adjusted computed results may be required to obtain a solution with minimum differences between the measured results and the computed results. However, an iterative solution of Equation (1) can converge to either one of the two possible solutions. When dealing with more than one voxel to reconstruct a realistic image, oscillation between the two possible values of $\mu$ at each voxel can result in an unstable iterative process. It will be appreciated that this problem becomes much more complex when a fan beam is utilized, wherein each detector measurement contains attenuation and scattering from several voxels within the field of view of the detector. Therefore, a forward-inverse numerical analysis algorithm applied to fan beams has been considered in the past as been practically unsolvable by any conventional ways.

Because of the diverging nature of radiation, a pencil beam per se is a theoretical expression only. It is believed that a pencil beam as described in the prior art, is in reality, a narrow cone beam and the attenuation and scattering contributed by voxels near the axis of the beam cannot be ignored. Therefore it is believed that a forward-inverse numerical analysis algorithm could have been used in the past in the field of density-imaging of objects, but with many approximations, assumptions and omissions.

As such, it is believed that a need exists for a new method and installation for single-side x-ray density-imaging of objects using a forward-inverse numerical analysis algorithm, wherein non-linearity of the problem is not an obstacle.

SUMMARY OF THE INVENTION

In the present invention, however, there is provided a method to transform a non-linear problem for x-ray backscatter imaging into a quasi-linear problem having a unique solution. In the method according to the present invention, the iterations which are carried out during the forward-inverse numerical analysis algorithm are effected using ratios of similar non-linear values.

Ratios are taken in such a way as to compare attenuation coefficients along comparable radiation beam paths in a pair of measurements. Because the transformed problem compares the discrepancy between calculated detector responses, non-linearity is no longer an issue. The inverse problem consequently, consists of matching calculated discrepancies. As a result, an image can be reconstructed by balancing relative errors.

Broadly, the method according to the present invention consists of irradiating an object with radiation beams selected from fan beams or cone beams, along a plurality of beam paths, and obtaining a plurality of measurements of radiation scattered out of the object from the beam paths, wherein each of the measurements has a linear influence due to scattering, a first exponential influence due to incident path attenuation and a second exponential influence due to scattering path attenuation. Pairs of measurements of scattered radiation having a similar origin within the object and similar first or second exponential influences are selected. A ratio is formulated for each pair of similar measurements, and the forward-inverse numerical analysis algorithm is solved iteratively using the ratios instead of the actual non-linear measurements. This method is advantageous in that such ratios reduce to a manageable level the duplicity of the solution due to non-linearity.

In another aspect of the method according to the present invention, the pair of measurements are selected such that their linear influences are also similar. The similarity in the linear and exponential influences in each pair of measurements ensures that the algorithm is partly constrained and that the iterative portion of the algorithm converges to a unique solution.

In yet another aspect of the method according to the present invention, the measurements of radiation scattered out of the object are taken with a detector that has a sight axis, and each of the aforesaid beam paths forms an acute angle with the sight axis. This method is particularly advantageous for imaging an object with one or more radiation sources and one or more detectors that are located on the same side of the object.

In a more detailed aspect of the present invention, there is provided a method for imaging an object using a forward-inverse numerical analysis algorithm. This method is effected using a source of radiation selected from x-rays, gamma rays or fast neutrons; and a radiation detector having a sight axis extending through the object of interest. The method comprises the steps of;

a) irradiating the object with a first beam of radiation extending along a first angle relative to the sight axis, and intersecting the sight axis along a segment of that axis, referred to herein as the scattering segment;

b) using the radiation detector, obtaining a first detector measurement of scattered radiation caused by the first beam;

c) irradiating the object with a second beam of radiation extending along a second angle relative to the sight axis, and intersecting the sight axis along the aforesaid scattering segment, the second angle being different from the first angle;

d) using the radiation detector, obtaining a second detector measurement of scattered radiation caused by the second beam;

e) formulating a first ratio with the first detector measurement and the second detector measurement, and working the forward-inverse numerical analysis algorithm using that ratio instead of individual detector measurements.

Taking a ratio of the actual detector measurements, as explained above, obviously prescribes the formulation of a ratio for the estimated detector measurements when working the forward-inverse numerical analysis algorithm, and therefore, the non-linearity of the inverse problem and the instability of the iterative process are greatly reduced.

In another aspect of the present invention, there is provided an apparatus for measuring the distribution of radiation attenuation coefficients through an object, from one side of the object, and for carrying out the aforesaid method. This apparatus has a first collimated detector having a first sight axis; a first radiation source having a first beam axis, wherein the first beam axis and the first sight axis extend along a same plane. The apparatus according to the present invention also comprises a second radiation source having a second beam axis, with this second beam axis also extending along the aforesaid same plane. The beam axes of the first and second radiation sources are spaced-apart from each other and are aligned to intersect the first sight axis along a same segment of that first sight axis. The detectors and the radiation sources are also movable in unison in a direction perpendicular to or parallel with the aforesaid plane to scan an object entirely from one side of that object. This apparatus is advantageous for producing attenuation-coefficient-related images of objects that are accessible from one side only.

This brief summary has been provided so that the nature of the invention may be understood quickly. A more complete understanding of the invention can be obtained by reference to the following detailed description of the preferred embodiments thereof in connection with the attached drawings.

BRIEF DESCRIPTION OF THE DRAWINGS

Several drawings are included to explain the method according to the preferred embodiment of the present invention and to illustrate an apparatus according to the preferred embodiment of the present invention, and in which.

DESCRIPTION OF THE PREFERRED EMBODIMENTS

Figure 1:
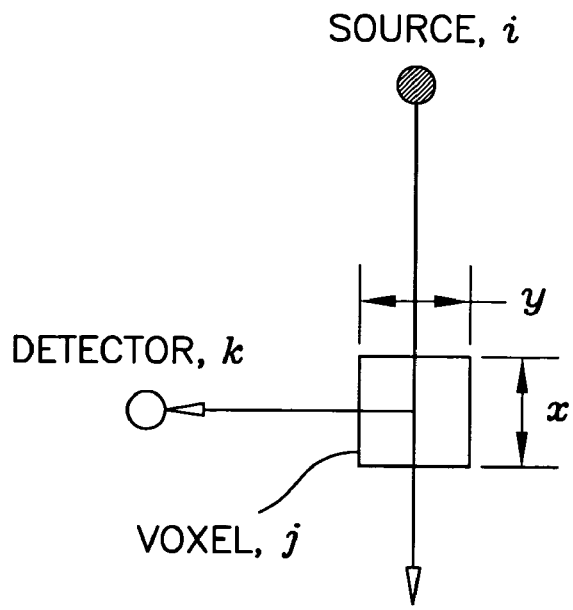
FIG. 1 is a schematic representation of a x-ray imaging system of the prior art.
Figure 2:
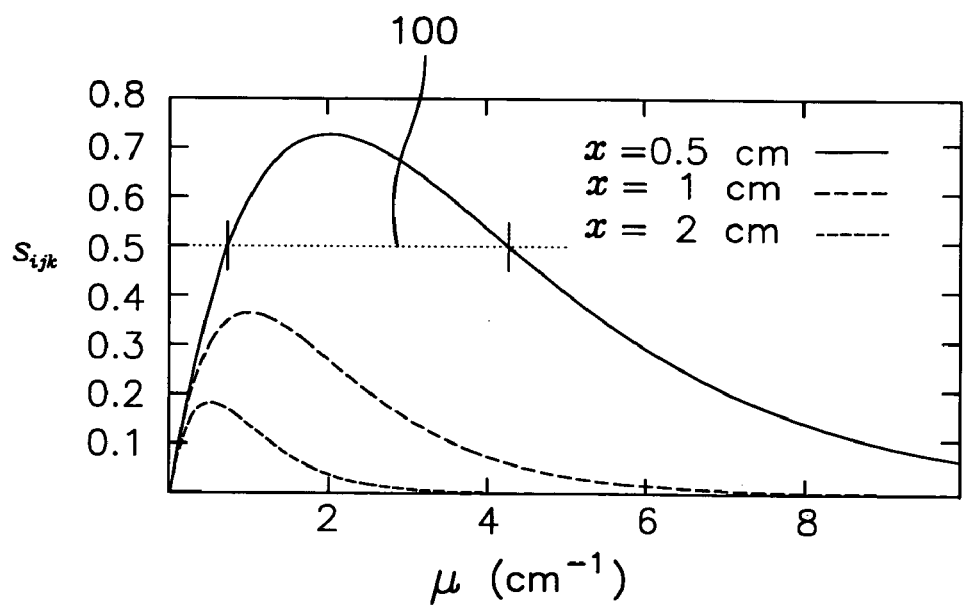
FIG. 2 is a graph showing the exponential relation between an attenuation coefficient $\mu$ and radiation transmission s at various depth x within an object irradiated by x-ray.

While this invention is susceptible of embodiments in many different forms, there are shown in the drawings and will be described in details herein one specific embodiment of a method to do x-ray imaging of thick objects from one side of the object and one preferred embodiment of an apparatus for x-ray imaging of objects, and for carrying out the preferred method. It should be understood that the present disclosure is to be considered as examples of the principles of the invention and is not intended to limit the invention to the embodiments illustrated and described. Furthermore, although x-ray and cone and fan beams are mentioned herein, it will be appreciated that the method and apparatus according to the preferred embodiments can also be used with pencil beams, with gamma rays and fast neutrons.

Similarly, it should also be appreciated, that the detector described herein can be collimated by physical means or by software means using energy measurement or time of flight measurement, for example, to determine origin and trajectory. Therefore the method described herein should not be limited by the way the detector axis is determined.

Figure 3:
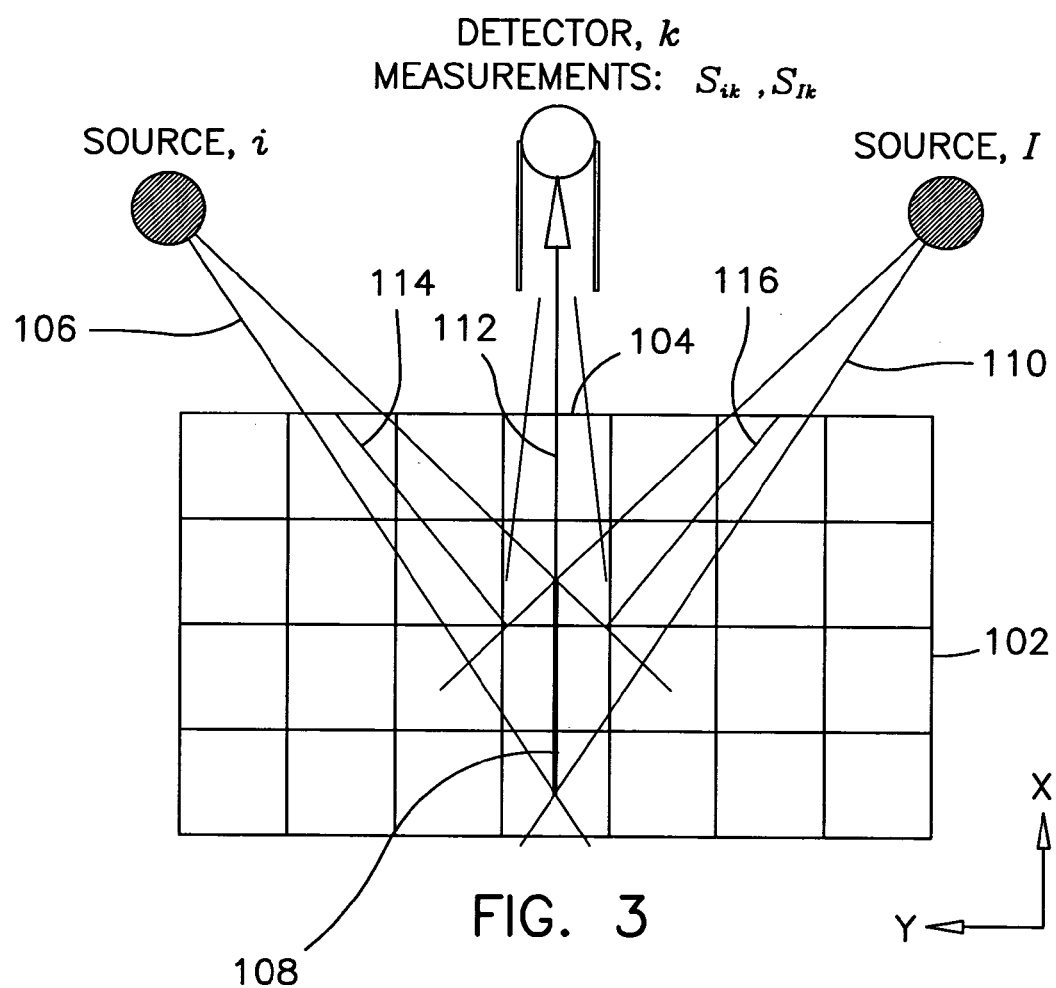
FIG. 3 is a 2-D schematic illustration of a x-ray imaging apparatus according to the preferred embodiment of the present invention.

A first schematic representation of the preferred apparatus to carry out the method according to the present invention is illustrated in FIG. 3. In this apparatus, an object to be examined is divided into a grid 102 of voxels, each having substantially a same size. A detector k is held fixed along one string 104 of voxels. A first collimated cone beam 106 of x-rays emitted from source i, is aligned to intersect the string 104 of voxels along a segment of scattering 108. Compton-scattering radiation emitted from this segment 108 are measured by the detector k. Detector k is collimated to reduce overlapping of the detected signal.

The expression Compton-scattering is used herein for convenience only and should not be used to limit the present invention to this type of radiation scattering to a detector.

A second cone beam 110 of x-rays emitted from a second source I is caused to traverse the grid 102 and to intersect the string 104 of voxels along the segment of scattering 108 mentioned above. Again, Compton-scattering radiation is measured by the detector k. It will be appreciated that a single cone beam 106, can be relocated to a second position to obtain the aforesaid second measurement. Similarly, it should be appreciated that a single source contributing to two complementary detectors can also be used, leading to a similar problem in which the solution is obtained for the distribution of the attenuation coefficient of the scattered radiation.

However, the use of two sources i, I with a common scattering path 112 to a same detector k, reduces the distance of travel from the scattering voxel to the detector site, and hence reduces the degree of attenuation at the lower photon energy of scattering. In all cases, scattered radiation from both sources i, I are measured one at a time. It will be appreciated that the sources i, I and detector k are moved to other positions relative to the object to obtain other pairs of measurements and to scan the object entirely.

In this system, the exiting path 112 of the scattered radiation from both sources is common. This exiting path 112 is also referred to herein as the sight axis of the detector k. Therefore, when a ratio of both detector measurements is taken, mainly the attenuations along incident paths 114, 116 are compared. The scattered radiation from both sources i, I and the attenuation along the exiting path 112 are similar in both measurements and therefore, these measurement influences are substantially reduced or practically cancelled out when taking the aforesaid ratio.

Furthermore, it will be appreciated that when only symmetrical sources are compared for single side inspection, a partially constrained system is developed, whereby a solution is more easily obtained. Therefore, in a preferred apparatus and method, both source beams define an angle that is centred on the sight axis of the detector.

The forward-inverse problem is solved by looking at the differences in attenuations along pairs of incident paths traversing the voxels leading to the segment of scattering 108. The transformed inverse problem consists of finding an image which forces the calculated relative measurement discrepancy to balance with the detector responses.

In the case of fan beams, it is understood that the exponential nature of the problem of radiation scattering forbids direct cancellation of common terms when comparing the responses of detectors that share common radiation paths. Nevertheless, taking such ratio tends to dampen the effect of the common terms and reduces the competition between the linear and exponential terms. Because the linear influences are gone and the non-linear influences are not dominant in the iterations, the method leads to the right solution. This aspect of the present invention is further expanded herein-below to demonstrate that the inverse problem can be transformed into a more stable domain.

Reference is briefly made again to prior art practices, in view of better explaining the method according to the preferred embodiment of the present invention. Conventional least-squares minimization applied to x-ray imaging is expressed as follows.

$$\text{minimize } u = \sum_{i=1}^{I} \sum_{k=1}^{K} [S_{ik}^* - S(\{\mu\})_{ik}]^2, \tag{3}$$

where $S_{ik}^*$ is the measured detector response and $S(\{\mu\})_{ik}$ is the estimated calculated detector response for some image with a distribution $\{\mu\}$ for source i and detector k and the summations are over all sources and detectors.

It should be noted that in the case of a fan beam or a cone beam, $S_{ik}$ for example, is the summation of all the voxels, j, in the field of view of the detector k, expressed as follows when referring to Equation (2):

$$S_{ik} = \sum_{j=1}^{n} s_{ijk} \tag{4}$$

Referring back to Equation (3), the objective of conventional least-squares minimization is to find the image $\{\mu\}$ that minimizes the difference between the recorded measurements and those calculated using the forward model of the problem. Due to the duality of solutions at a given voxel, however, it will be appreciated that the objective function of Equation (3) has local optima that compete with each other preventing the convergence to a common global optimum. A modified objective function that compares similar relative measurements is therefore used.

In the method according to the preferred embodiment, the following function is introduced:

$$\text{minimize } u_1 = \sum_{i=1}^{I} \sum_{k=1}^{K} \left[\frac{S_{Ik}^*}{S_{ik}^*} - \frac{S_{Ik}}{S_{ik}}\right]^2 \tag{5}$$

where the ratio between two measurements for a pair of sources i and I at a given detector k; expressed as $S_{Ik}^*/S_{ik}^*$ is to be matched with the calculated ratio, $S_{Ik}/S_{ik}$ of corresponding calculated detector responses at a given image distribution $\{\mu\}$.

The method according to the preferred embodiment also works when comparing a first ratio of a calculated detector response for one source over a corresponding detector measurement, with another ratio of the other calculated detector response for the other source in the same pair of measurement, over the other corresponding detector measurement, as expressed as follows:

$$\text{minimize } u_2 = \sum_{i=1}^{I} \sum_{k=1}^{K} \left[\frac{S_{Ik}}{S_{Ik}^*} - \frac{S_{ik}}{S_{ik}^*}\right]^2 \tag{6}$$

Image reconstruction proceeds progressively from one approximation to another using an iterative approach. That is, a solution is found for $\{\Delta\mu\}$, the vector difference between two successive approximations, $$\text{where } \Delta\mu = \mu^{l+1} - \mu^l \tag{7}$$

and l indicate a particular iteration, by solving the matrix equation:

$$R = [D]\Delta\mu, \tag{8}$$

where the $m^{th}$ entry of vector R, corresponding to source i, its complement source I and detector k, is given by, $$r_m = \left(\frac{S_{Ik}}{S_{Ik}^*} - \frac{S_{ik}}{S_{ik}^*}\right) \tag{9}$$

[D] is a matrix, in which an element $d_{mj}$ is given by:

$$d_{mj} = \frac{d}{d\mu_j}\left(\frac{S_{ik}}{S_{ik}^*} - \frac{S_{Ik}}{S_{Ik}^*}\right) \tag{10}$$

where m defines a particular pair of sources, i, I, contributing to a certain detector, k, and the derivative is taken with respect to the estimated attenuation coefficient of voxel j.

In essence, the formulation of Equation (8) attempts to balance the relative error between calculated detector responses (forward model) and measured detector responses (inverse problem).

When inverting Equation (8), a smoothing regularization constraint is preferably incorporated in the equation to assist the image reconstruction process. This regularization constraint causes neighbouring voxels to have similar properties. This is accomplished by adding a function that penalizes the roughness of a reconstructed image. In the application of this constraint, it is assumed that a physical solution is relatively smooth. The regularization function states that each voxel's value should be similar to that of its surrounding voxels or;

$$\text{minimize } p = \sum_{j=1}^{N}\left(\mu_j - \sum_{q=1}^{n}\frac{\mu_{h(j,q)}}{n}\right)^2 \quad (11)$$

This equation dictates that the attenuation coefficient of voxel j equals the average attenuation coefficient of the n voxels surrounding it. Hence, the function h(j,q) provides the index number of the $q^{th}$ voxel adjoining voxel j. Applying regularization in the preferred method produces:

$$\text{minimize } u_3 = \sum_{m=1}^{M} w_m\left(r_m - \sum_{j=1}^{N} d_{mj}\mu_j^{l+1} + \sum_{j=1}^{N} d_{mj}\mu_j^l\right) + \gamma\sum_{j=1}^{N}\left(\mu_j^{l+1} - \sum_{q=1}^{n}\frac{\mu_{h(j,q)}^{l+1}}{n}\right) \quad (12)$$

where $w_m$ and $\gamma$ are scaling weighting values; $w_m$ is the weight given to the $m^{th}$ measurement ratio and $\gamma$ is the weight given to the regularization matrix. This can be expressed in matrix form as $$[D]^T[W]\{\{R\}+[D]\{\mu\}_l\} = [[D]^T[W][D]+\gamma[G]]\{\mu\}_{l+1} \quad (13)$$

where [G] is the regularization matrix based solely on grid geometry.

Image reconstruction is conducted iteratively wherein for example, the successive approximation solution at iteration l+1 then becomes:

$$\{\mu\}_{l+1} = [[D]^T[W][D]+\gamma[G]]^{-1}[D]^T[W]\{\{R\}+[D]\{\mu\}_l\} \quad (14)$$

where [W] is a diagonal weighting function, with each element corresponding to the weight given to each ratio of detector responses, γ is a regularization parameter or weight, and [G] is a matrix that relates each voxel to adjacent neighbours and as such solely depends on the grid geometry of the voxels imposed on the image. Superscript T indicates matrix transposition.

In the preferred method, a lower bound is imposed on the solution whereby non-positive values of μ are set to zero, since they are not physically allowed, and can skew the iterative process considerably due to the exponential nature of the forward mapping. In addition, an upper bound for the value μ, is imposed so that the exponential term in the forward model does not become insignificant. This upper limit is equal to 0.45 cm$^{-1}$ which is about twice the attenuation coefficient in water, for a 102 keV x-ray source, for example.

Because of the exponential nature of the forward problem, an infinite attenuation coefficient can produce zero detector response. The same result can, however, be produced with a zero value of attenuation coefficient due to the linear term in the forward problem.

In order to limit the number of iterations in the forward-inverse numerical analysis algorithm, the theoretical values in the forward problem should be related to the attenuation coefficients that are expected to be found in the material being studied. These theoretical values should be estimated according to the energy of the source beam and other physical conditions present, such as object geometry and materials, and the quality and amount of data available. Preferably, the theoretical values should be set as close as possible from the attenuation coefficients that are expected to be found.

In addition to binding the theoretical values, it is also preferable to introduce a regularization factor in the forward-inverse numerical analysis algorithm. When attempting to reconstruct an image without regularization, the behaviour of the iterative process can be erratic, and the reconstructed image can be quite noisy with image features that are barely identifiable. However, a small amount of regularization stabilizes the problem considerably, and causes a significant decrease in the condition number of the inverted matrix [D] thereby ensuring its non-singularity.

It has been found that a value of γ of 0.5 or higher and preferably 2 to 4 provides substantial stability to the problem with a 102 keV x-ray source. It should be noted that a γ value of about 30 causes the smoothing matrix [G] in Equation (14) to have about the same amount of influence on the solution as the system response matrix $[D^T][W][D]$. The drastic stabilization with a small value of γ was found to be attributed to the role of regularization plays in imposing order on the problem.

Without regularization, the first estimate of {μ} could be quite drastically different from the actual solution. Since the matrix [D] of Equation (13) is constructed based on the value of {μ} in the previous iteration, the matrix [D] could also be affected by the noise. This effect would be carried through from one iteration to another, leading the problem astray. Additional regularization leads to smoothness of the image, without further severely affecting the structure of the system response matrix.

Having explained the theory and parameters of the method according to the preferred embodiment of the present invention, this preferred method is described hereinbelow in step form, and in greater details related to the forward-inverse numerical analysis algorithm.

In one aspect of the present invention, the preferred method for imaging an object using radiation selected from x-rays, gamma rays or fast neutrons, comprises the steps of:

a) providing a first collimated radiation detector pointing at the object; the collimated detector having a sight axis extending through the object;

b) providing means for irradiating the object with one or more radiation beams having a shape selected from a pencil beam, a fan beam or a cone beam;

c) irradiating the object with a first radiation beam having a first beam path intersecting the sight axis of the first detector along a first segment of that sight axis; the first segment being selected so that the detector can detect a non-zero measurement;

d) using the first detector, obtaining a first actual detector measurement of radiation scattered by the object from the first radiation beam;

e) irradiating the object with a second radiation beam having a second beam path different from the first beam path; the second beam path intersecting the sight axis of the detector along the first segment of the sight axis;

f) using the first detector, or a second detector at a second location, obtaining a second actual detector measurement of radiation scattered by the object along the first segment from the second radiation beam;

g) associating the first and second actual detector measurements with the first and second beam paths respectively;

h) moving the object relative to the detector, or moving the beam paths relative to the sight axis of the detector or relative to each other such that an intersection thereof with the sight axis is a second common segment different from the first segment;

i) repeating the steps of irradiating, obtaining, associating and moving, and obtaining first and second actual detector measurements for each of a second and subsequent pairs of actual detector measurements of radiation scattered by the object corresponding respectively to first and second beam paths in each of a second and subsequent pairs of beam paths, until all voxels in the object have been intersected at least twice by the beam paths;

j) using matrix manipulation and image reconstruction algorithms, calculating corrected radiation attenuation coefficients of the object along each of the beam paths; relating the radiation attenuation coefficients to density values and constructing a density image of the object, or relating the attenuation coefficients to visual indicators and constructing an attenuation-coefficient image of the object, wherein the method also comprises the following steps which are carried out simultaneously with the step of obtaining first and second actual detector measurements;

k) defining first and second guessed radiation attenuation coefficients through the object along a corresponding pair of beam paths;

l) using the first and second guessed radiation attenuation coefficients, calculating first and second estimated detector measurements corresponding to the guessed radiation attenuation coefficients along the corresponding pair of beam paths;

m) comparing a first ratio of the first and second estimated detector measurements with a second ratio of the pair of actual detector measurements for the corresponding pair of beam paths or, comparing a first ratio of the first estimated detector measurement and the first actual detector measurement for the first beam path in the corresponding pair of beam paths with a second ratio of the second estimated detector measurement and the second actual detector measurement for the second beam path in the corresponding pair of beam paths, and obtaining a difference between the first and second ratios;

n) using the difference, correcting the first and second guessed radiation attenuation coefficients, o) repeating the steps of calculating, comparing and correcting, and obtaining first and second corrected radiation attenuation coefficients along the first and second beam paths in the corresponding pair of beam paths respectively.

The method according to the preferred embodiment of the present invention was tested using fan beams 106, 110 having a diverging angle of about 5°. The results have demonstrated that the preferred method is quite robust, as the calculations converged smoothly to an acceptable solution. The calculations converged smoothly, in spite of some initial instability in the matching of calculated detector responses with actual measurements. For error-free detector responses, the inversion was nearly perfect. Even with highly disturbed detector responses, a reasonable image was obtained.

Figure 4:
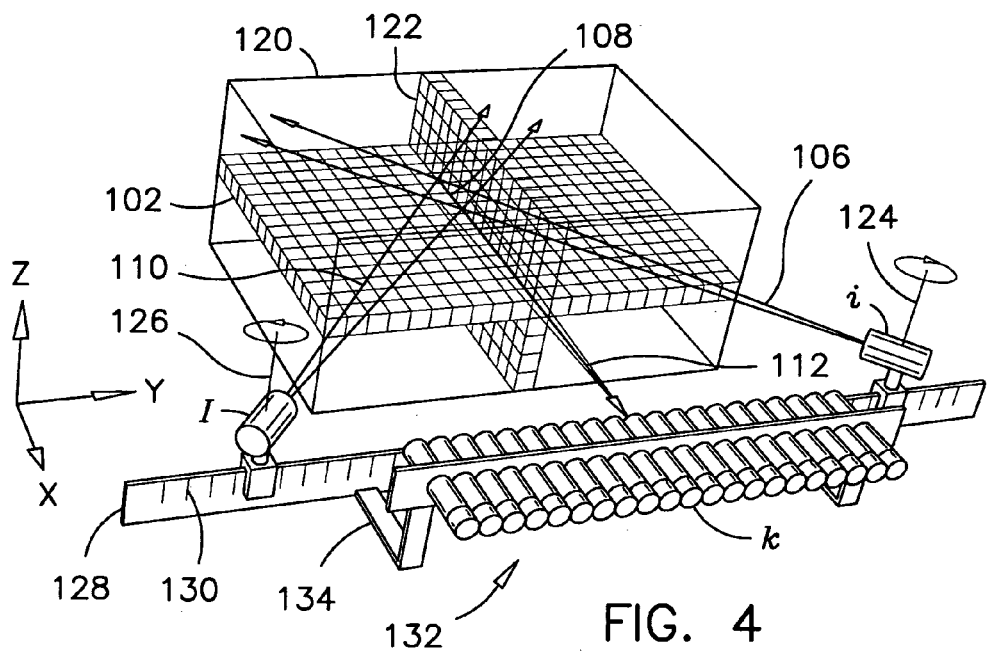
FIG. 4 is a 3-D schematic illustration of the x-ray imaging apparatus according to the preferred embodiment of the present invention.

Referring now to FIG. 4, an image reconstruction in 3D can be achieved by stacking grids 102 of the 2D problem as illustrated in FIG. 3, over each other. These grids 102 are referred to as the X-Y problem, and together form a volume 120. In use, each X-Y slice 102 is exposed to radiation, with fan or cone beam sources i, I in a manner similar to that of FIG. 3. It will be understood that the fan or cone beam sources i, I and the axis of a detector k are aligned along a same plane extending along a X-Y slice.

The source-detector assembly is then moved one voxel level in the Z direction, and another set of measurements is acquired for the adjacent X-Y grid of voxels. This procedure is then repeated for the rest of the volume 120. Once the volume has been covered, the entire process is preferably repeated for the same volume 120 but using Z-X slices 122 instead of X-Y slices 102 to obtain additional measurements.

During the scanning process, the sources i, I are rotated about their respective Z axes 124, 126 to sweep the beams 106, 110 along each of the X-Y slices. The sources i, I are also moved between measurements on a rail 128 for example, extending along the Y axis. The sources i, I are preferably moved by increments 130 of one voxel's width at the time.

In the preferred apparatus, a linear array 132 of juxtaposed collimated detectors k are mounted on a frame 134 which is also affixed to the aforesaid rail 128 such that the radiation sources i, I are movable along the array 132 of detectors k, and remain aligned within a same plane as defined by the field of view of the detectors in the array 132.

In use, the entire assembly of detectors k and sources i, I, the rail 128 and the frame 134 are movable in the Z direction as a single unit relative to the object 120, to scan the entire object 120.

The scanning of the object 120 along the Y and the Z axes doubles the number of independent measurements. In practice, it is preferable to over-determine the forward-inverse problem by ensuring that each voxel in the object 120 to be examined is traversed by one of the incident beams 106, 110 at least twice and preferably four times.

Figure 5:
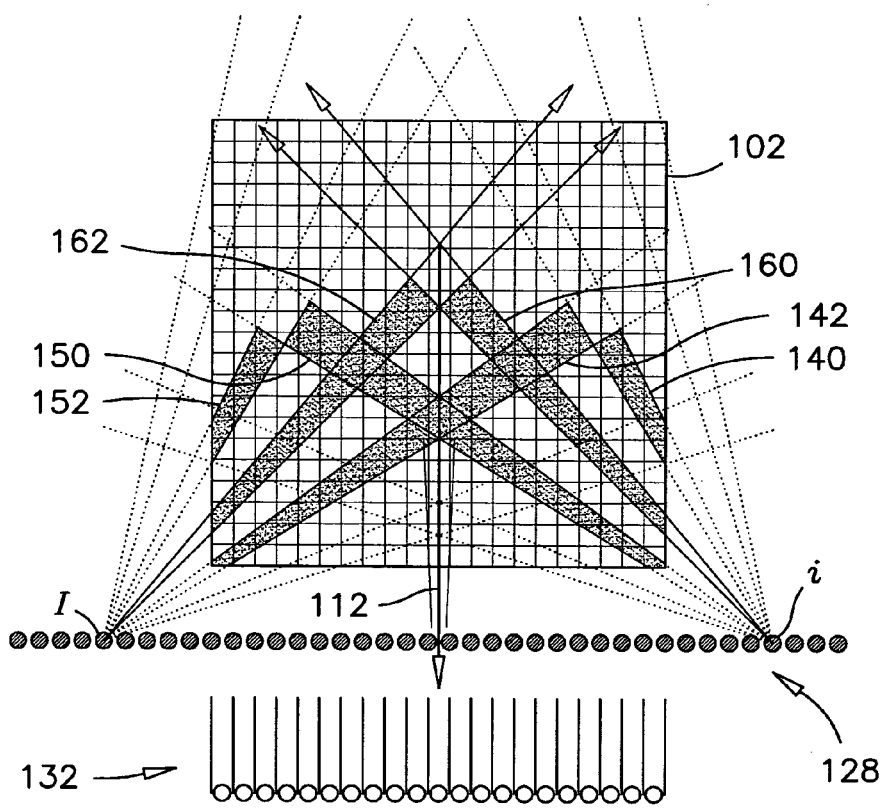
FIG. 5 is a plan view of a slice in an object being scanned with the apparatus according to the preferred embodiment; illustrating pairs of incident beams along which voxel's attenuation coefficients are obtained and by which image reconstruction is effected.

Referring now to FIG. 5, it will be appreciated that the method according to the preferred embodiment is carried out to obtain corrected attenuation coefficients along the incident beam pairs, such as those labelled as 140–142; 150–152; 160–162 or 142–150, etc., and along every beam pair covering the sectors in-between. The beam pairs in the method according to the preferred embodiment do not need to form complementary angles or symmetrical angles related to the detector's axis 112. The symmetry shown in FIGS. 3–5 is for convenience only.

The calculations to relate attenuation coefficients to density, and the trigonometry used to reconstruct of a density image of the object are not explained herein because these techniques are not the focus of the present invention.

While the preferred embodiment of a method and a preferred embodiment of an apparatus according to the present invention have been illustrated and described herein above, it will be appreciated by those skilled in the art that various modifications, alternate constructions and equivalents may be employed without departing from the true spirit and scope of the invention. Therefore, the above description and the illustrations should not be construed as limiting the scope of the invention which is defined by the appended claims.

What is claimed is:

1. A method for imaging an object using x-ray, gamma rays or fast neutrons; and a forward-inverse numerical analysis algorithm, comprising the steps of;

irradiating said object with radiation beams selected from fan beams or cone beams, along a plurality of beam paths;

obtaining a plurality of measurements of radiation scattered out of said object from said beam paths, wherein each of said measurements has a linear influence, a first exponential influence and a second exponential influence related to a density of said object;

selecting pairs from said measurements having a similar origin within said object and similar first or second exponential influences;

taking a ratio of each of said pairs of said measurements;

iteratively solving said forward-inverse numerical analysis algorithm using said ratios instead of said measurements; and reconstructing an image of said object using corrected attenuation coefficients corresponding to said first or second exponential influences.

2. The method as claimed in claim 1, wherein said measurements of radiation scattered out of the object are taken with a detector having a sight axis, and each of said beam paths forms an acute angle with said sight axis.

3. The method as claimed in claim 1, wherein each of said pair of measurements have similar linear influences.

4. The method as claimed in claim 1, wherein said second exponential influences are related to incident radiation penetrating said object, and said first exponential influences are related to scattering radiation exiting said object.

5. The method as claimed in claim 4, wherein said step of selecting is effected with pair of said measurements having similar said first exponential influences and said step of reconstructing is effected with attenuation coefficients corresponding to said second exponential influences.

6. The method as claimed in claim 4, wherein said step of obtaining is effected using a collimated detector, and said similar origin is a segment along a sight axis of said collimated detector.

7. A method for imaging object using radiation selected from x-rays, gamma rays and fast neutrons; a source of said radiation, a radiation detector having a sight axis extending through said object and a forward-inverse numerical analysis algorithm; comprising the steps of;

irradiating said object with a first beam of radiation extending along a first angle relative to said sight axis, and intersecting said sight axis along a first scattering segment;

using said radiation detector, obtaining a first detector measurement of scattering radiation caused by said first beam;

irradiating said object with a second beam of radiation extending along a second angle relative to said sight axis and intersecting said sight axis along said first scattering segment, said second angle being different from said first angle;

using said radiation detector, obtaining a second detector measurement of scattering radiation caused by said second beam;

formulating a first ratio with said first and second detector measurements;

calculating first and second calculated detector responses;

making a second ratio with said calculated detector responses;

iteratively balancing relative errors between said first and second ratios and calculating corrected radiation attenuation coefficients of said object alone said first and second beams and said segment; and relating said corrected radiation attenuation coefficients to visual indicators and constructing an attenuation-coefficient image of said object along said first and second beams and said segment.

8. The method as claimed in claim 7, wherein said first and second angles are mirror angles relative to said sight axis.

9. The method as claimed in claim 7 wherein said step of balancing relative errors includes the step of adding a regularization constraint thereto causing each of said voxels in a same region of said object to have similar properties.

10. The method as claimed in claim 7 further including the steps of dividing said object into voxels and repeating said steps of irradiating said object along first and second angles; obtaining first and second detector measurements; and formulating a ratio with said first and second detector measurements; with second and subsequent beam pairs and second and subsequent scattering segments until each of said voxels is intersected at least four times by said beams of radiation.

11. The method as claimed in claim 10, further including the steps of identifying all voxels in a field of view of said detector during each of said detector measurements, and constructing an image of said object using attenuation coefficient through each of said voxels.

12. A method for imaging an object using radiation selected from x-rays or gamma rays, comprising the steps of:

a) providing a collimated radiation detector pointing at said object; said collimated detector having a sight axis extending through said object;

b) providing means for irradiating said object with one or more radiation beams having a shape selected from a pencil beam, a fan beam or a cone beam;

c) irradiating said object with a first radiation beam having a first beam path intersecting said sight axis of said detector along a first segment of said sight axis; said first segment being selected so that said detector detects a non-zero measurement;

d) using said detector, obtaining a first actual detector measurement of radiation scattered by said object from said first radiation beam;

e) irradiating said object with a second radiation beam having a second beam path different from said first beam path; said second beam path intersecting said sight axis of said detector along said first segment of said sight axis;

f) using said detector, obtaining a second actual detector measurement of radiation scattered by said object from said second radiation beam;

g) associating said first and second actual detector measurements with said first and second beam paths respectively;

h) moving said object relative to said detector, or moving said beam paths relative to said sight axis of said detector or relative to each other such that an intersection thereof with said sight axis is a second common segment different from said first segment;

i) repeating said steps of irradiating, obtaining, associating and moving, and obtaining first and second actual detector measurements for each of a second and subsequent pairs of actual detector measurements of radiation scattered by said object corresponding respectively to first and second beam paths in each of a second and subsequent pairs of beam paths, until all voxels in said object have been intersected at least twice by said beam paths;

while obtaining each of said pairs of actual detector measurements;

defining first and second guessed radiation attenuation coefficients through said object along a corresponding pair of beam paths;

using said first and second guessed radiation attenuation coefficients, calculating first and second estimated detector measurements corresponding to said guessed radiation attenuation coefficients along said corresponding pair of beam paths;

comparing a first ratio of said first and second estimated detector measurements with a second ratio of said pair of actual detector measurements for said corresponding pair of beam paths or, comparing a first ratio of said first estimated detector measurement and said first actual detector measurement for said first beam path in said corresponding pair of beam paths with a second ratio of said second estimated detector measurement and said second actual detector measurement for said second beam path in said corresponding pair of beam paths, and obtaining a difference between said first and second ratios;

using said difference, correcting said first and second guessed radiation attenuation coefficients, repeating said steps of calculating, comparing and correcting, and obtaining first and second corrected radiation attenuation coefficients along said first and second beam paths in said corresponding pair of beam paths respectively; and j) using matrix manipulation and image reconstruction algorithms, relating said corrected radiation attenuation coefficients to density values and constructing a density image of said object, or relating said corrected radiation attenuation coefficients to visual indicators and constructing an attenuation-coefficient image of said object.

13. The method as claimed in claim 12, wherein said first and second beam paths form symmetrical angles relative to said detector axis.

14. The method as claimed in claim 12, wherein said detector measurements having a zero value are eliminated from said step of repeating said steps of calculating, comparing and correcting, and obtaining.

15. An apparatus for measuring radiation attenuation coefficients of material inside an object, comprising:

a first collimated detector having a first sight axis;

a first radiation source having a first beam axis, said first beam axis and said first sight axis extending along a same plane;

a second radiation source having a second beam axis, said second beam axis also extending along said same plane and said first and second radiation sources and said first collimated detector being on a same side of said object;

said beam axes being non-parallel with each other and being aligned to intersect said first sight axis along a same segment of said first sight axis.

16. The apparatus as claimed in claim 15, further comprising means for varying orientations of said first and second radiation beams within said same plane.

17. The apparatus as claimed in claim 16, further comprising a plurality of collimated detectors having a second and subsequent sight axes parallel with said first sight axis and extending along said same plane.

18. The apparatus as claimed in claim 17, further including means for moving said detectors, said radiation sources and said plane in unison.

19. The apparatus as claimed in claim 15, further including means for moving said radiation sources along said plane.

* * * * *